US00PP32739P2

(12) United States Plant Patent
Probst

(10) Patent No.: US PP32,739 P2
(45) Date of Patent: Jan. 5, 2021

(54) ***COREOPSIS* PLANT NAMED 'BUTTER RUM'**

(50) Latin Name: ***Coreopsis* hybrid**
Varietal Denomination: Butter Rum

(71) Applicant: Darrell R Probst, Hubbardston, MA (US)

(72) Inventor: Darrell R Probst, Hubbardston, MA (US)

( * ) Notice: Subject to any disclaimer, the term of this patent is extended or adjusted under 35 U.S.C. 154(b) by 0 days.

(21) Appl. No.: 16/873,311

(22) Filed: Mar. 18, 2020

(51) Int. Cl.
*A01H 5/02* (2018.01)
*A01H 6/14* (2018.01)

(52) U.S. Cl.
USPC ..... Plt./417
CPC ..... *A01H 6/14* (2018.05)

(58) Field of Classification Search
USPC ..... Plt./417
CPC ..... A01H 5/02
See application file for complete search history.

*Primary Examiner* — Kent L Bell
(74) *Attorney, Agent, or Firm* — Penny J. Aguirre

(57) ABSTRACT

A new cultivar of hybrid *Coreopsis* plant named 'Butter Rum' that is characterized by its sturdy, well-branched plant habit reaching an average of 42 cm in height and 60 cm in width, its floriferous and long blooming season of nearly sterile inflorescences that do not require deadheading; bloom commences in early July and lasts until frost in Kensington, Conn., its medium sized inflorescences with ray florets that are yellow in color with red flushed tips, its near sterility, its resistance to powdery mildew (*Podosphaera macularis*) and leafspot (*Pseudomonas cichorii*), and its cold hardiness at least to U.S.D.A. Zone 5a.

2 Drawing Sheets

Botanical classification: *Coreopsis* hybrid.
Variety denomination: 'Butter Rum'.

BACKGROUND OF THE INVENTION

The present invention relates to a new and distinct cultivar of *Coreopsis* plant, botanically of hybrid origin and known as *Coreopsis* 'Butter Rum' and will be referred to hereinafter by its cultivar name, 'Butter Rum'. The new cultivar of *Coreopsis* is an herbaceous perennial grown for landscape and container use.

The new Invention arose from an ongoing controlled breeding program in New Braintree, Mass. The objective of the breeding program is to develop hybrid cultivars of *Coreopsis* with unique and superior garden attributes. In particular, to develop cultivars that are long-lived, sturdy, exhibit a true perennial habit and cold hardy to at least U.S.D.A. Zone 5 in a wide range of flower colors and plant forms that do not require vernalization to intiate flowering.

The Inventor made a controlled cross in August of 2015 in New Braintree, Mass. between an unnamed and unpatented proprietary plant from his breeding program as the female parent and pollen that was pooled from a variety of unnamed and unpatented proprietary plants from his breeding program as the male parent. The exact characteristics of the pollen parent are therefore unknown. 'Butter Rum' was selected in September of 2016 as a single unique plant amongst the resulting seedlings.

Asexual propagation of the new cultivar was first accomplished by stem cuttings under the direction of the Inventor in Kensington, Conn. in September of 2016. Asexual propagation by stem cuttings has shown that the characteristics of the new cultivar are stable and are reproduced true to type in successive generations.

SUMMARY OF THE INVENTION

The following traits have been repeatedly observed and are determined to be the characteristics of the new cultivar.

These attributes in combination distinguish 'Butter Rum' as a unique cultivar of *Coreopsis*.

1. 'Butter Rum' exhibits a sturdy, well-branched plant habit reaching an average of 42 cm in height and 60 cm in width.
2. 'Butter Rum' exhibits a floriferous and long blooming season of nearly sterile inflorescences that do not require deadheading; bloom commences in early July and lasts until frost in Kensington, Conn.
3. 'Butter Rum' exhibits medium sized inflorescences with ray florets that are yellow in color with red flushed tips.
4. 'Butter Rum' exhibits resistance to powdery mildew (*Podosphaera macularis*) and leafspot (*Pseudomonas cichorii*).
5. 'Butter Rum' is nearly sterile and seeds have rarely been observed.
6. 'Butter Rum' exhibits cold hardiness at least to U.S.D.A. Zone 5a.

The female parent of 'Butter Rum' differs from 'Butter Rum' in having inflorescences with ray florets that are copper in color, in not being reliably hardy in U.S.D.A. Zone 5, in having a taller plant height and more upright plant habit, and in being very fertile. 'Butter Rum' can be most closely compared to *Coreopsis* cultivars 'Route 66' (U.S. Plant Pat. No. 20,609) and 'Sassy Saffron' (U.S. Plant Pat. No. 31,393). Both are similar to 'Butter Rum' in having thread-leaf type foliage, inflorescences with ray florets that are primarily yellow in color, and similar cold hardiness. Both differ from 'Butter Rum' in having inflorescences with ray florets that have a red colored eye zone and in being very fertile with an abundance of seed produced.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosure and/or sales prior to the filing date but less than one year prior to the effective filing date. Publications include but are not limited to website listings by Bluestem perennials, Skagit Horticulture, Emerald Coast Growers, Prides Corner Farms, Santa Rosa Gardens, Mill Creek Plants, and Hirt's Gardens.

BRIEF DESCRIPTION OF THE DRAWINGS

The accompanying colored photographs illustrate the overall appearance and distinct characteristics of the new *Coreopsis*. The photographs were taken of a 4-month-old plant from a 30 cell sized plug of 'Butter Rum' as grown outdoors in a 1-gallon container in Kensington, Conn.

The photograph in FIG. 1 provides a side view of 'Butter Rum' and shows the plant habit in bloom.

Figure 1:
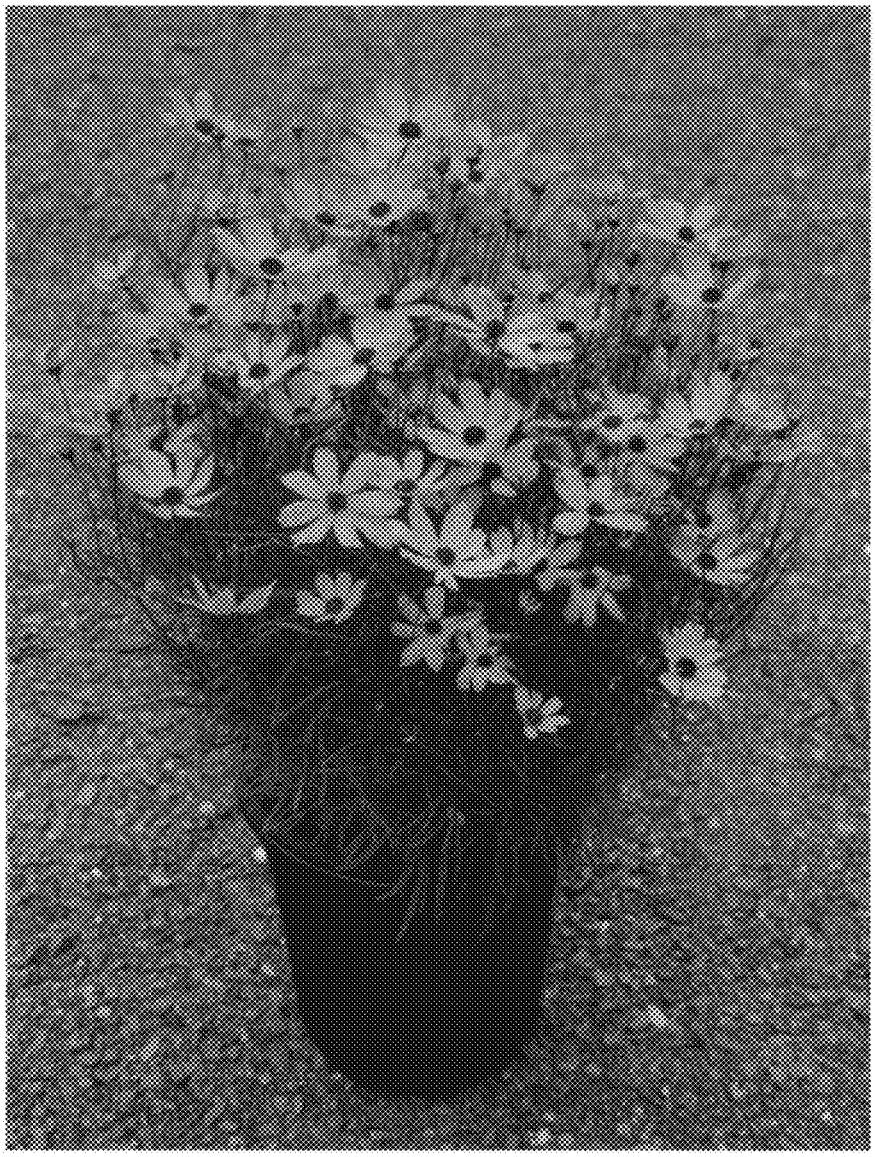
Figure 2:
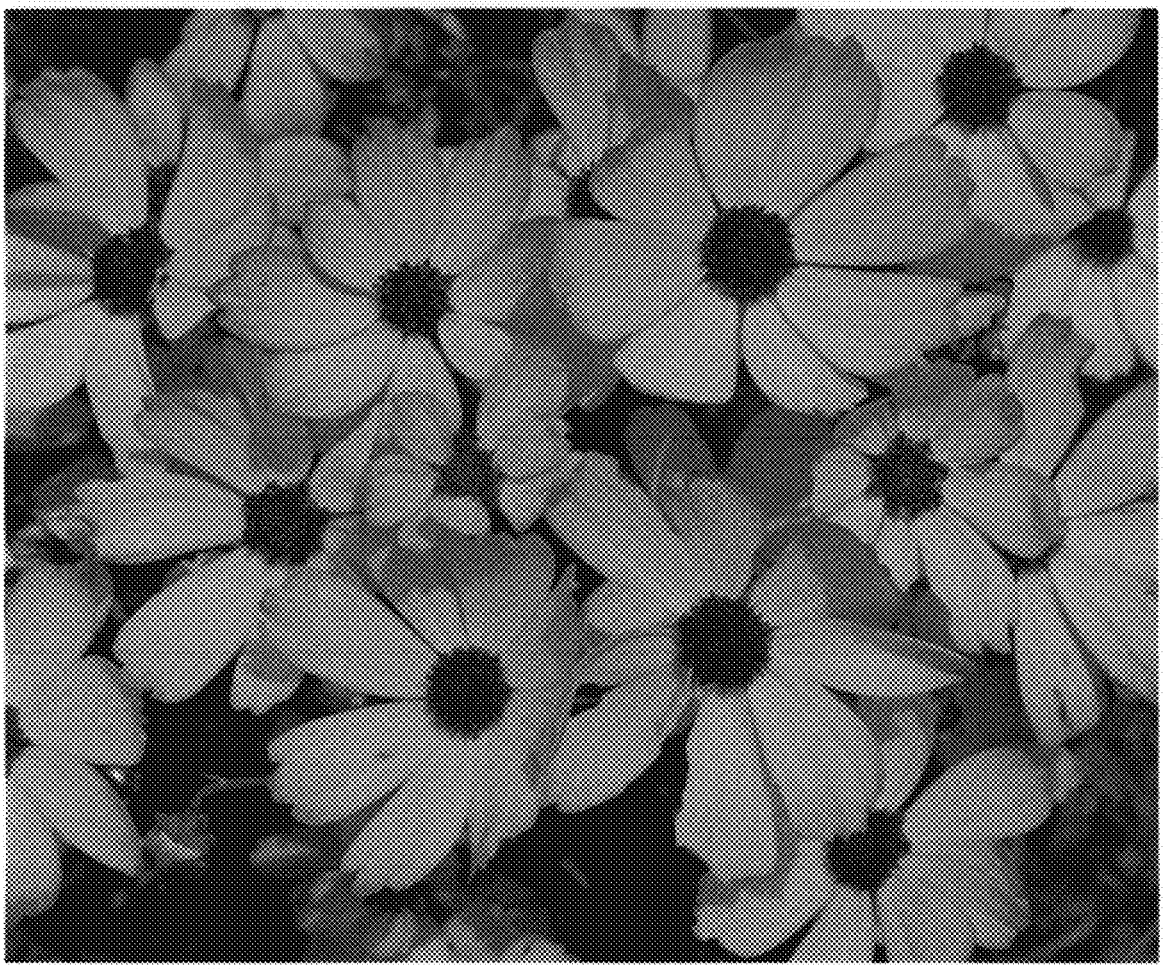

The photograph in FIG. 2 provides a close-up view of the inflorescences of 'Butter Rum'.

The colors in the photographs are as close as possible with the photographic and printing technology utilized and the color values cited in the detailed botanical description accurately describe the colors of the new *Coreopsis*.

DETAILED BOTANICAL DESCRIPTION

The following is a detailed description of 3-month-old plants of 'Butter Rum' as grown outdoors in one-gallon containers in Kensington, Conn. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period*.—Blooms from early July until frost in Kensington, Conn.

*Plant type*.—Herbaceous perennial.

*Plant habit*.—Clump-forming, compact, upright leafy flowering stems with inflorescences held above the foliage.

*Height and spread*.—Reaching an average of 42 cm in height and 60 cm in width as grown in the landscape.

*Cold hardiness*.—At least to U.S.D.A Zone 5a.

*Diseases and pests*.—Resistance to powdery mildew (*Podosphaera macularis*) and leafspot (*Pseudomonas cichorii*), no susceptibility or resistance to pests has been observed.

*Root description*.—Fibrous and fine, NN155A in color.

*Propagation*.—Stem cuttings.

*Time required for root initiation*.—An average of 10 days for root initiation.

*Growth rate*.—Vigorous.

Stem description:

*Shape*.—Rounded to tetragonal, solid.

*Stem color*.—146A.

*Stem strength*.—Strong.

*Stem size*.—Main stems; an average of 6 cm in length and 5 mm in width, lateral stems; 10 to 14 cm in length (excluding peduncles) and 2 to 3 mm in width.

*Stem surface*.—Glabrous, smooth, and dull.

*Branching habit*.—Freely branched, an average of 5 basal main stems, lateral stems typically branched as oppositely arranged pairs at each node, with an average of 6 lateral stems (2 pairs) per main stem.

*Internode length*.—An average of 4 cm.

Foliage description:

*Leaf division*.—Simple.

*Leaf margins*.—Entire and trifid.

*Leaf size*.—Entire leaves; an average of 6 cm in length and 5 cm in width, trifid leaves; center lobe an average of 5.5 cm in length and 2 mm in width, lateral lobes an average of 3 cm in length and 1 mm in width.

*Leaf shape*.—Narrow obanceolate.

*Leaf base*.—Cuneate.

*Leaf apex*.—Bluntly acute.

*Leaf venation*.—Pinnate, inconspicuous, same color as leaf.

*Leaf attachment*.—Sessile.

*Leaf arrangement*.—Opposite.

*Leaf surface*.—Upper and lower surfaces; smooth, dull, and glaucous.

*Leaf color*.—Young and mature upper and lower surface; 137A.

Flower description:

*Inflorescence type*.—Composite with a single row of ray florets surrounding disc florets in the center, forming a radiant head, inflorescences are borne on branch terminals in loose corymbs.

*Lastingness of inflorescence*.—8 to 10 days until senescence of ray florets, phyllaryies and disc florets are persistent.

*Fragrance*.—Very faint pleasant scent.

*Quantity of inflorescences*.—Free flowering, an average of 26 corymbs per main branch, an average of 3 composites per corymb.

*Inflorescence size*.—Corymbs; an average of 10 cm in length and 5 cm in width, composite; an average of 2 cm in depth and 4 cm in diameter with disc portion up to 8 mm in diameter.

*Inflorescence buds*.—Globose in shape, an average of 5 mm in depth and diameter, smooth and shiny surface; color; a blend of 143A and N144A, streaks of 165A held at the margins.

*Peduncle*.—Rounded in shape, strong, an average of 8 cm in length and 1 mm in diameter, 147A in color, smooth and glabrous surface.

Phyllaries (involucral bracts):

*Phyllary number*.—2 rows; outer (lower) row 7, inner (upper) row 8.

*Phyllary arrangement*.—Outer (lower) phyllaries; 10% fused, held horizontal to slightly upwards with the apex and mid-section recurved downwards, inner (upper) phyllaries; overlap and surround receptacle with apical portion reflexed (campanulate-like).

*Phyllary size*.—Outer (lower) phyllaries; an average of 4 mm in length and 1 mm in width, inner (upper) phyllaries; an average of 6 mm in length and 4 mm in width.

*Phyllary color*.—Upper and lower surfaces, outer (lower) phyllaries; 143A, margins 142B, inner (upper) phyllaries; transluscent, 17A, margins flushed with N167A, very tip 166A.

*Phyllary texture*.—Outer (lower) phyllaries; glabrous and smooth on both surfaces, inner (upper) phyllaries; glabrous and slightly waxy on both surfaces.

*Phyllary apex*.—Acute.

*Phyllary base*.—Truncate.

*Phyllary shape*.—Outer (lower) phyllaries; elliptic to lanceolate, inner (upper) phyllaries; lanceolate.

Ray florets (sterile):

*Number*.—8.

*Shape*.—Oblanceolate, with the appearance of 3 longitudinal sections.

*Size*.—An average of 1.5 cm in length and 6 mm in width.

*Apex*.—Rounded with three rounded lobes.

*Base*.—Cuneate.

*Margins*.—Entire on sides with lobed and notched apex.

*Aspect*.—Held mainly horizontal and slightly upwards, perpendicular to peduncle.

*Texture*.—Both surfaces; glabrous, dull, and satiny.

*Color*.—Upper and lower surfaces when opening; 9A, upper surfaces when fully open; 9A, flushed with a blend of 172A and N172A on the tips to mid-section, lower surfaces when fully open; 9A, margins flushed with 172A, all surfaces fading to 21A before drop.

Disc florets (male and female):

*Number*.—An average of 120.

*Shape*.—Tubular, corolla is fused, flared and slightly curled at apex.

*Size*.—About 7 mm in length and 0.5 mm in width.

*Color*.—En masse; a blend of 165A, 154A and N163A, corolla; (tube) base and mid-section transluscent, 22A, top below flare 202A, flared portion N163A.

*Receptacle*.—An average of 6 mm in diameter and 1 mm in depth, 147A in color.

Reproductive organs:

*Presence*.—Disc florets only.

*Gynoecium*.—1 Pistil; an average of 5 mm in length, style; very fine and 10D in color, bifid pillose, stigma; N163A in color with recurved branches about 0.5 mm in length, ovary is inferior, oblong in shape, an average of 2 mm in length and 1 mm in width, and 165A in color.

*Androecium*.—4 stamens, fused into tube surrounding style, an average of 3 mm in length and less than 0.5 mm in width, 202A in color, no pollen was present.

*Seed*.—Seed development has been observed to be very minimal; nearly sterile, plants available for data collection did not set seed.

It is claimed:

1. A new and distinct cultivar of *Coreopsis* plant named 'Butter Rum' as herein illustrated and described.

* * * * *